United States Patent [19]
Farrell et al.

[11] Patent Number: 6,001,872
[45] Date of Patent: Dec. 14, 1999

[54] WATER SOLUBLE TRANSPLATINUM COMPLEXES WITH ANTI-CANCER ACTIVITY AND METHOD OF USING SAME

[75] Inventors: Nicholas P. Farrell, Richmond, Va.; Ulrich Bierbach, Saint Paul, Minn.

[73] Assignee: Virginia Commonwealth University, Richmond, Va.

[21] Appl. No.: 09/263,222

[22] Filed: Mar. 5, 1999

[51] Int. Cl.$^6$ ............................. A61K 31/28; C07F 15/00
[52] U.S. Cl. ............................. 514/492; 556/137; 546/5; 546/6; 548/104; 548/105; 548/402; 548/403
[58] Field of Search ............................. 514/492; 556/137; 546/5, 6; 548/104, 105, 402, 403

[56] References Cited

U.S. PATENT DOCUMENTS

| | | | |
|---|---|---|---|
| 4,937,358 | 6/1990 | Bitha et al. | 549/206 |
| 4,996,337 | 2/1991 | Bitha et al. | 556/137 |
| 5,107,007 | 4/1992 | Farrell | 556/137 |
| 5,562,925 | 10/1996 | Rosenberg et al. | 424/649 |
| 5,585,511 | 12/1996 | Yokoi et al. | 556/137 |
| 5,665,771 | 9/1997 | Murrer | 514/492 |

OTHER PUBLICATIONS

Sigel, Astrid and Sigel, Helmut, Metal Ions in Biological Systems, 1996, vol. 32, pp. 603–639.

*Primary Examiner*—Mukund J. Shah
*Assistant Examiner*—Pavanaram K Sripada
*Attorney, Agent, or Firm*—Whitham, Curtis & Whitham

[57] ABSTRACT

The present invention relates to the treatment of tumors with a novel water soluble trans-platinum coordination compound having the general structural formula $[PtBX_m(NR^*_3)]$ where B is a planar, heterocyclic ring containing at least one nitrogen atom, and a pendant chelating group; and X is an anionic ligand; and R* is hydrogen or a lower alkyl.

18 Claims, No Drawings

WATER SOLUBLE TRANSPLATINUM COMPLEXES WITH ANTI-CANCER ACTIVITY AND METHOD OF USING SAME

BACKGROUND OF THE INVENTION

1. Field of the Invention

The present invention generally relates to water soluble trans-Pt (II) complexes, their synthesis routes, and their methods of use as anti-cancer agents.

2. Background Description

The use of cisplatin, cis-[PtCl$_2$(NH$_3$)$_2$], and carboplatin, [Pt(CBDCA)(NH$_3$)$_2$] (CBDCA=1,1-cyclobutanedicarboxylate), in the treatment of certain cancers is well-established. Nevertheless, there is a continued interest in the design of structurally novel platinum compounds that show antitumor activity complementary to that of the clinical drugs. The fact that transplatin, trans-[PtCl$_2$(NH$_3$)$_2$],

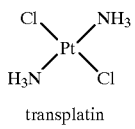

transplatin was found to be therapeutically inactive, has been considered a paradigm for the structure-activity relationships (SAR) of platinum(II) antitumor compounds; trans-Pt compounds have been dismissed as ineffective in vivo agents.

However, the presence of a planar ligand such as pyridine or quinoline, e.g., in trans-[PtCl$_2$(NH$_3$)(quinoline)],

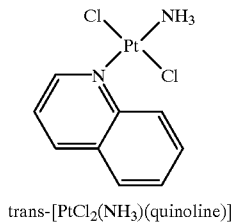

trans-[PtCl$_2$(NH$_3$)(quinoline)]

dramatically enhances the in vitro cytotoxicity of the trans geometry. The cytotoxic activity of such "nonclassical" trans-platinum complexes has been discussed in terms of both an overall altered affinity toward biologically relevant (N and S) nucleophiles and unique DNA binding modes.

The above "nonclassical" trans-platinum species has, however, been found to have limited bioavailability and, consequently, low in vivo activity. One possible explanation is lack of solubility. It would be clearly desirable to design a trans-platinum species that retains the property of cytotoxicity and yet is water-soluble, thereby enhancing its bioavailability and potential in vivo usefulness for the treatment of tumors.

SUMMARY OF THE INVENTION

It is an object of the present invention to provide a trans-Pt compound (containing a planar ligand) with high water solubility and bioavailability. More particularly, the present invention relates to a method of treating a mammal afflicted with a tumor using such a trans-Pt compound. The cytotoxic activity of the Pt compound of this invention has been experimentally established by studies that are described in the Examples herein.

DETAILED DESCRIPTION OF A PREFERRED EMBODIMENT OF THE INVENTION

The present invention relates to a method of treating tumors in mammals. In particular, the method comprises administering to a patient an amount of a compound having the general structural formula:

[PtBX$_m$(NR*$_3$)]

wherein B represents a planar, heterocyclic ring (such as thiazole, benzothiazole, quinoline, isoquinoline, acridine, imidazole, oxazole or pyrazine) containing: 1) at least one N atom (to coordinate the metal) and 2) a pendant chelating group (such as carboxylates [RCOO-, where R=CH$_3$, C$_2$H$_5$, or other lower alkyls] phosphonates, or sulfonates) that is available to chelate the metal center through one of the oxygen atoms of the group; and wherein R*=represents a hydrogen or lower alkyl moiety (e.g., C$_{1-12}$ alkyl) and each of the R* constituents can be the same or different (e.g. NH$_3$, NH$_2$R* or NR*$_2$H); and X represents an anionic ligand such as halogens (Cl, Br, or I), alkoxides (e.g. OR where R=CH$_3$, C$_2$H$_5$, or other lower alkyls), sulfhydryls (SR where R=CH$_3$, C$_2$H$_5$, or other lower alkyls), nitrates (NO$_3$), perchlorates (ClO$_4$) and carboxylates (RCOO- where R=CH$_3$, C$_2$H$_5$, etc.).; and where m=1 or 2, depending on the protonation state of B (when B is protonated, m=2; when B is deprotonated, m=1.) The geometry of the complex is trans for NH$_3$ related to the nitrogen atom of B that is covalently bonded to Pt, and the square-planar entity is electroneutral.

Pathway 1, shown below, depicts the synthetic pathway that leads to one specific embodiment of the complex, trans-[Pt(PyAc-N,O)Cl(NH$_3$)] (complex 2).

Pathway 1

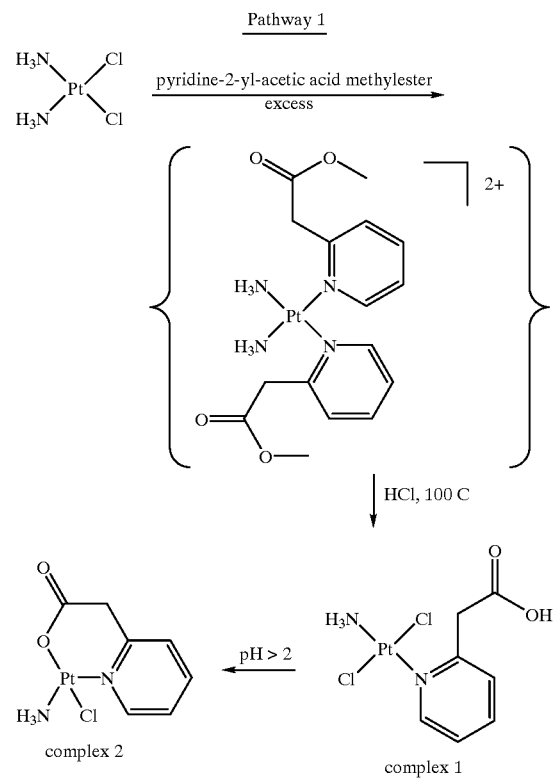

complex 2 complex 1

The details of this synthesis may be found in Example 1 below. The preparation utilizes the anionic N,O-chelating ligand pyridine-2-yl-acetate (PyAc), which introduces a carboxylate donor cis to the nitrogen atom of the planar ligand. The bidentate ligand was used in its O-protected form, i.e., the corresponding methylester (PyAcMe). Formation of the N,O-chelate was achieved via the intermediate dichloro form, trans-[PtCl$_2$(NH$_3$)(PyAcH)].H$_2$O (complex 1.H$_2$O) at neutral pH. The displacement of chloride in complex 1 by carboxylate under the above conditions (e.g. in 10$^{-2}$ M HCl) is remarkably facile.

Complexes 1 and 2 were characterized by means of $^1$H NMR and IR spectroscopy and elemental analyses. In addition, a single crystal X-ray structure analysis of complex 2 was performed. In the solid state, complex 2 consists of discrete, neutral complex molecules that are packed with weak intermolecular hydrogen bonding interactions (O1 . . . N2 296(1) pm, O2 . . . N2 329(1) pm). In complex 2, platinum exhibits a square-planar, [N$_2$OCl] environment with the expected trans-coordination of the N-donors. The Pt-N, Pt-O, and Pt-Cl distances are in the usual range observed for divalent platinum.

Bond angles around the metal only marginally deviate from 90° and 180°, respectively, which suggests a strainless coordination of the PyAc ligand. In the solid state, the six-membered chelate ring in complex 2 adopts a boat-like, folded conformation, which is characterized by an angle of ca. 70° between planes through the atoms Pt-N1-C2-C7 and Pt-O1-C8-C7. The $^1$H NMR spectrums of complex 2 and complex 4 in [d$_7$]DMF show a sharp singlet for the methylene protons (C7), suggesting a high degree of structural flexibility of the N,O-chelate and rapid interconversion of different conformations in solution. The improved solubility (4 mmol 1$_{-1}$) of the target compound complex 2 in water, compared to analogous complexes trans-[PtCl$_2$(NH$_3$)L], may be ascribed to the hydrogen-bond acceptor properties of the carboxylate group. A similar increase in solubility of platinum complex is observed when replacing both chloro-ligands in cisplatin with a dicarboxylate ligand, e.g. in carboplatin.

The cytotoxic properties of complex 2 and its geometric isomer, cis-[Pt (PyAc-N,O)Cl (NH$_3$)] were investigated. The most striking feature of the two isomers proved to be their distinct cytotoxicities, as monitored by cell-growth inhibition experiments in murine L1210 leukemia (Example 2). Preliminary data show that, in vitro, the trans-isomer complex 2 is comparably cytotoxic to cisplatin itself, whereas surprisingly, the cis-isomer has to be considered inactive.

The present study is the first to demonstrate a trans-geometry requirement for an active platinum complex.

It has been noted above that complex 2 is readily formed from complex 1 at pH values greater than 2. For the purposes of this invention, it should be further noted that the form for administration to patients may be either complex 1 or complex 2, since the former would spontaneously form the N-O chelate under physiological conditions.

Implementation of the claimed invention will generally involve identifying patients suffering from tumors and administering the platinum coordination compound in an acceptable form by an appropriate route. The dosage to be administered may vary, depending on the age, gender, weight and overall health status of the individual patient, as well as the nature of the cancer itself.

Administration can be oral or parenteral, including intravenously, intramuscularly, subcutaneously, etc., or by other routes (e.g. transdermal, sublingual, etc.).

The compounds can be administered in the pure form or in a pharmaceutically acceptable formulation including suitable elixirs, binders, and the like or as pharmaceutically acceptable salts or other derivatives. It should be understood that the pharmaceutically acceptable formulations and salts include liquid and solid materials conventionally utilized to prepare injectable dosage forms and solid dosage forms such as tablets and capsules. Water may be used for the preparation of injectable compositions which may also include conventional buffers and agents to render the injectable composition isotonic. Solid diluents and excipients include lactose, starch, conventional disintergrating agents, coatings and the like. Preservatives such as methyl paraben or benzalkium chloride may also be used. Depending on the formulation, it is expected that the active composition will consist of 1–99% of the composition and the vehicular "carrier" will constitute 1–99% of the composition.

While complex 2, set forth above, has the structural formula PtBX$_m$(NH$_3$), it appears that the important feature is the use of a planar heterocyclic ring trans to nitrogen of the amine moiety. Therefore, it will be understood by those of skill in the art that the amine group can be substituted with lower alkyls (i.e., C$_{1-12}$ alkyl moities) instead of hydrogens. Therefore, the compounds which can be used in the practice of this invention fall within the general structural formula PtBX$_m$(NR*$_3$) defined above.

In the following examples, objects and advantages of this invention are further illustrated by various embodiments thereof but the details of those examples should not be construed to unduly limit this invention. In Example 1, Pyridine-2-yl-acetic acid methylester (PyAcMe) was prepared from pyridine-2-yl-acetic acid hydrochloride (Aldrich), according to standard esterification methods. $^1$H NMR spectra (300 MHz) were taken at 295 K in [D$_7$]DMF with TMS standard.

All parts and percentages are by weight unless otherwise indicated.

EXAMPLES

Example 1 trans-[Pt(PyAc-N,O)Cl(NH$_3$)] was synthesized and characterized in the following manner:

Complex 1.H$_2$O: A mixture of 1.791 g (5.96 mmol) of cisplatin and 2.700 g (17.88 mmol) of pyridine-2-yl-acetic acid methylester was heated in 100 mL of water at 90–100° C. for 2 h. To the solution were added 18 mL of conc. HCl, and heating was continued for 5 h. Concentration of this mixture to a volume of 20 mL and storage at 4° C. afforded complex 1.H$_2$O as a bright-yellow crystalline solid, which was filtered off and washed with EtOH and Et$_2$O. Yield 1.290 g (50%) $^1$H NMR: δ=3.53 (crystal H$_2$O), 4.20 (br s, 3 H, NH$_3$), 4.20 (s, 2 H, CH$_2$), 7.43 (t, 1 H, H5), 7.68 (d, 1 H, H3), 7.96 (t, 1 H, H4), 8.92 (d, 1 H, H6), 13.06 (br s, 1 H, CO$_2$H). IR (KBr): ν(C=O) 1716 cm$^1$. C,H,N analysis: Calcd.: C 19.19, H 2.76, N 6.39; found: C 19.29, H 2.50, N 6.30.

Complex 2: To a solution of 1.000 g of Na$_2$HPO$_4$ in 50 mL of water (pH~9) were added 0.500 g (1.14 mmol) of complex 1.H$_2$O, and the mixture was heated at 50° C. until all of the platinum complex was dissolved (less than 5 min). Complex 2 precipitated spontaneously as fme, off-white needles, which were collected after the reaction mixture had cooled to room temperature and finally recrystallized from 10$^{-2}$ M HCl. Yield 0.290 g (66%) of pale-yellow prisms. $^1$H NMR: δ=4.07 (s, 1 H, CH$_2$), 4.53 (br 5, 3 H, NH$_3$), 7.50 (t, 1 H, H5), 7.62 (d, 1 H, H3) , 8.08 (t, 1 H, H4) , 8.91 (d, 1 H, H6). IR (KBr): ν(C=O) 1647 cm$^{-1}$. C,H,N analysis: Calcd.: C 21.90, H 2.36, N 7.30; found: C 21.88, H 2.36, N 7.25.

Example 2

Studies were performed in vitro to assess the cytotoxicity of trans-[Pt(PyAc-N,O)Cl(NH$_3$)] in comparison to several relevant Pt compounds. Cytotoxicity was monitored by cell-growth inhibition experiments in murine L1210 cisplatin-sensitive leukemia cells. The L1210 cell line has been used as a prognosticator of human antitumor activity for some time [Wolpert-DeFilippes, M. K., "Antitumor Activity of Cisplatin Analogs" in: *Cisplatin. Current Status and Developments*, Prestayko, A. W., Crooke, S. T., and Carter, S. K., eds, Academic Press, (London) 1980, pp. 183–192.]. A separate, non-treated culture was used as a control for these investigations.

The results are set forth in Table 1, which shows the $ID_{50}$ (50% inhibitory drug concentration ) for 72-hour drug incubations of the compounds trans-[Pt(PyAc-N,O)Cl(NH$_3$)], its cis-isomer cis-[Pt(PyAc-N,O)Cl(NH$_3$)], the well-known "classical" anti-tumor compound cisplatin, and transplatin, which is known to be biologically inactive.

TABLE 1

| Compound | $ID_{50}$ |
| --- | --- |
| trans-[Pt(PyAc-N,O)Cl(NH$_3$)] | 0.88 µM |
| cis-[Pt(PyAc-N,O)Cl(NH$_3$)] | >20 µM |
| cisplatin | 0.43 µM |
| transplatin | 14 µM |

It is apparent from the results that trans-[Pt(PyAc-N,O)Cl(NH$_3$)] is comparably cytotoxic to cisplatin itself. In contrast, the cis-isomer (like transplatin) must be considered inactive.

While the invention has been described in terms of its preferred embodiments, those skilled in the art will recognize that the invention can be practiced with modification within the spirit and scope of the appended claims.

We claim:

1. A platinum coordination compound having the general formula:

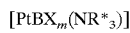

wherein,

X is an anionic ligand, m is 1 or 2,

R* is selected from the group consisting of hydrogen and lower alkyls and each of the R* constituents can be the same or different, B is a planar, heterocyclic ring moiety containing at least one nitrogen atom as a ring member, and a pendant chelating group, and a nitrogen atom of B is covalently bonded to Pt and is trans- to NR*$_3$.

2. The compound of claim 1 wherein said planar, heterocyclic ring moiety is selected from the group consisting of: pyridines, thiazoles, benzothiazoles, quinolines, isoquinolines, acridines, imidazoles, oxazoles and pyrazines.

3. The compound of claim 2 wherein said planar, heterocyclic ring moiety is a pyridine.

4. The compound of claim 1 wherein said pendant chelating group is selected from the group consisting of: carboxylates, $(CH_2)_nCOO^-$, where n=1–3; phosphonates, $(CH_2)_nP(OR)O_2^-$, where n=1–3 and R is a lower alkyl; and sulfonates, $(CH_2)_nSO_3^-$, where n=1–3.

5. The compound of claim 4 wherein said pendant chelating group is $CH_2COO^-$.

6. The compound of claim 1 wherein X is selected from the group consisting of: halogens, $NO_3$, $ClO_4$, alkoxides (OR), sulfhydryls (SR) and carboxylates ($RCOO^-$), where R is a lower alkyl.

7. The compound of claim 5 wherein X is chloride.

8. The compound of claim 1 wherein said Pt coordination compound is trans-[Pt(PyAc-N,O)Cl(NH$_3$)], having the formula:

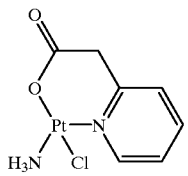

9. The compound of claim 1 wherein said Pt coordination compound is trans-[PtCl$_2$(NH$_3$)(PyAcH)].H$_2$O.

10. A pharmaceutical composition for the treatment of tumors in patients, comprising a platinum coordination compound having the general formula:

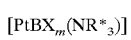

wherein,

X is an anionic ligand, m is 1 or 2,

R* is selected from the group consisting of hydrogen and lower alkyls and each of the R* constituents can be the same or different, B is a planar, heterocyclic ring moiety containing at least one nitrogen atom as a ring member, and a pendant chelating group, a nitrogen atom of B is covalently bonded to Pt and is trans- to NR$_3$, and a suitable pharmaceutical carrier.

11. The pharmaceutical composition of claim 9 wherein said Pt coordination compound is trans-[Pt(PyAc-N,O)Cl(NH$_3$).

12. The pharmaceutical composition of claim 9 wherein said Pt coordination compound is trans-[PtCl$_2$(NH$_3$)(PyAcH)].H$_2$O.

13. A method of preparing a trans-platinum compound having the general formula:

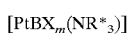

wherein,

X is an anionic ligand, m is 1 or 2,

R* is selected from the group consisting of hydrogen and lower alkyls and each of the R* constituents can be the same or different, B is a planar, heterocyclic ring moiety containing at least one nitrogen atom as a ring member, and a pendant chelating group, and a nitrogen atom of B is covalently bonded to Pt and is trans- to NR*$_3$, comprising the steps of:

forming a mixture of cisplatin and a heterocyclic chelating ligand;

reacting said mixture at high temperature; and precipitating said trans-platinum compound by adjusting the pH of said mixture.

14. A method of preparing a trans-platinum compound having the formula:

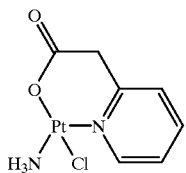

comprising the steps of:
heating a mixture having 40% by weight cisplatin and 60% by weight pyridine-2-yl-acetic acid methylester in water at 90–100° C.
adding concentrated HCl to said mixture and continuing heating;
reducing by evaporation the volume of this mixture by 80%;
filtering and washing in ethanol/diethyl ketone a yellow crystalline solid; and
dissolving said yellow crystalline solid in a solution of $Na_2HPO_4$ and water with heating.

15. A method for treating tumors in patients, comprising the step of administering to a patient in need thereof an effective amount of a platinum coordination compound of the general formula:

$$[PtBX_m(NR^*_3)]$$

wherein,

X is an anionic ligand, m is 1 or 2,

R* is selected from the group consisting of hydrogen and lower alkyls and each of the R* constituents can be the same or different, B is a planar, heterocyclic ring containing at least one nitrogen atom as a ring member, and a pendant chelating group, and a nitrogen atom of B is covalently bonded to Pt and is trans to $NR_3$.

16. The method of claim 14 wherein said Pt coordination compound is trans-[Pt(PyAc-N,O)Cl(NH$_3$)].

17. The method of claim 14 wherein said Pt coordination compound is trans-[PtCl$_2$ (NH$_3$)(PyAcH)].H$_2$O.

18. The method of claim 14 wherein said step of administration is oral or parenteral.

* * * * *